(12) United States Patent
Backstrom et al.

(10) Patent No.: US 8,372,824 B2
(45) Date of Patent: *Feb. 12, 2013

(54) GABA-STEROID ANTAGONISTS AND THEIR USE FOR THE TREATMENT OF CNS DISORDERS

(75) Inventors: Torbjorn Backstrom, Umeå (SE); Per Lundgren, Umeå (SE); Ming-De Wang, Umeå (SE)

(73) Assignee: Umecrine AB, Umea (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/372,389

(22) Filed: Feb. 13, 2012

(65) Prior Publication Data

US 2012/0142657 A1  Jun. 7, 2012

Related U.S. Application Data (63) Continuation of application No. 11/791,160, filed as application No. PCT/SE2005/001671 on Nov. 7, 2005, now Pat. No. 8,114,860.

(60) Provisional application No. 60/629,511, filed on Nov. 18, 2004.

(51) Int. Cl.
  A61K 31/56 (2006.01)
  A61P 25/00 (2006.01)
(52) U.S. Cl. ........................ 514/169; 514/789
(58) Field of Classification Search ............. 514/169, 514/789
  See application file for complete search history.

(56) References Cited

U.S. PATENT DOCUMENTS

| 4,614,499 | A | 9/1986 | Arseneault et al. | |
|---|---|---|---|---|
| 8,114,860 | B2 * | 2/2012 | Backstrom et al. | 514/169 |
| 2003/0125311 | A1 | 7/2003 | Baulieu et al. | |

FOREIGN PATENT DOCUMENTS

| WO | 99/45931 A1 | 9/1999 |
|---|---|---|
| WO | 01/68068 A2 | 9/2001 |
| WO | 03/059357 A1 | 7/2003 |
| WO | 2006/054938 A1 | 5/2006 |

OTHER PUBLICATIONS

Non-Final Office Action received for U.S. Appl. No. 11/791,160, mailed on Jan. 31, 2011, 14 pages.
Notice of Allowance received for U.S. Appl. No. 11/791,160, mailed on Oct. 6, 2011, 8 pages.
International Search Report received for PCT Patent Application No. PCT/SE2005/001671 mailed on Feb. 21, 2006, 6 pages.
International Preliminary Report on Patentability received for PCT Patent Application No. PCT/SE2005/001671 completion on Mar. 9, 2007, 14 pages.
Francis et al., "Reversed-phase high-performance liquid chromatography of C21 metabolites of progesterone", Journal of Chromatography, vol. 336, No. 1, 1984, pp. 361-367.
Prince et al., "Differential Antagonism by Epipregnanolone of Alphaxalone and Pregnanolone Potentiaion of [3H] Flunitrazenpam Binding Suggests More Than the One Class of Binding Site for Steroids at GABAA Receptors", Neuropharmacology vol. 32, No. 1, 1993, pp. 59-63.
Wang et al., "3β-Hydroxypregnane Steroids are Pregnanolone Sulfate-Like GABAA Receptor Antagonists", The Journal of Neuroscience vol. 22 No. 9, May 2002, pp. 3366-3375.

* cited by examiner

*Primary Examiner* — Jennifer M Kim
(74) *Attorney, Agent, or Firm* — Morrison & Foerster LLP (57) ABSTRACT

Compounds exhibiting 3alpha-hydroxy-5alpha/beta-steroid blocking action with no or only low antagonism against the gamma-aminobutyric acid (A) receptor (GABA-A), and compounds exhibiting partial antagonism against said receptor are presented. Methods for the prevention, treatment and/or alleviation of various CNS-disorders are suggested, as well as pharmaceutical compositions for such use.

6 Claims, 2 Drawing Sheets

GABA-STEROID ANTAGONISTS AND THEIR USE FOR THE TREATMENT OF CNS DISORDERS

CROSS REFERENCE TO RELATED APPLICATIONS

This application is a Continuation of U.S. patent application Ser. No. 11/791,160, with a filing date of Oct. 30, 2007, (Now U.S. Pat. No. 8,114,860), which is the National Stage of International Patent Application of PCT/SE2005/001671, filed Nov. 7, 2005, which claims the benefit of U.S. Provisional Patent Application Ser. No. 60/629,511, filed Nov. 18, 2004, each of which is hereby incorporated by reference in its entirety.

The present invention concerns the treatment, alleviation or prevention of GABA-steroid related and/or induced disorders of the central nervous system (CNS), and in particular specific steroid compounds for this purpose, their use for the manufacture of pharmaceuticals for said treatment, as well as methods of treatment involving their use.

BACKGROUND OF THE INVENTION

The metabolites of the sex and stress hormones pregnenolone, progesterone, desoxycortico-sterone, cortisone and cortisol, known as pregnanolones; as well as the metabolites of testosterone, androstendione and dehydroepiandrosterone, have all been the subject of various studies, at least partially elucidating their role in the neurological signal system in mammals.

The steroids inducing CNS symptoms and disorders of interest in the present application all have a structural similarity in comprising a 3alpha-hydroxy group, a 5alpha or 5beta pregnane steroid body, and a ketone or hydroxy group on position 17, 20 or 21.

Steroids comprising 3alpha-hydroxy-5alpha/beta-pregnan-20-one/ol or 3alpha-hydroxy-5alpha/beta-androstan-17-one/ol have been shown to be important specific enhancers of the gamma-aminobutyric acid (A) receptor (GABA-A). They bind to the GABA-A receptor and act by enhancing the effect of GABA in terms of the opening frequency of the GABA-A receptor and its opening duration. The effect is similar to the effects of both benzodiazepines and barbiturates. Said steroid compounds however have a binding site separate from that of both these compounds. Examples of such GABA enhancing steroids and their number according to the Chemical Abstracts Registry/Chicago Academy of Science (CAS) are given in Table 1.

The steroid nomenclature is not entirely consistent, and therefore the nomenclature developed by the International Union of Pure and Applied Chemistry (IUPAC) will be used throughout this application.

TABLE 1

Nomenclature of GABA-steroids

| IUPAC-nomenclature | CAS Number |
|---|---|
| 3alpha-hydroxy-5alpha-pregnan-20-one | 516-54-1 |
| 3alpha-hydroxy-5beta-pregnan-20-one | 128-20-1 |
| 3alpha,21-dihydroxy-5alpha-pregnan-20-one | 567-02-2 |
| 3alpha,21-dihydroxy-5beta-pregnan-20-one | 567-03-3 |
| 3alpha,11beta,17alpha,21-tetrahydroxy-5beta-pregnan-20-one | 53-02-1 |
| 3alpha-11beta,17alpha,21-tetrahydroxy-5alpha-pregnan-20-one | 302-91-0 |
| 3alpha-17alpha,21-trihydroxy-5alpha-pregnan-11,20-dione | 547-77-3 |
| 3alpha-17alpha,21-trihydroxy-5beta-pregnan-11,20-dione | 53-05-4 |
| 3alpha-hydroxy-5alpha-androstan-17beta-ol | 1852-53-5 |
| 3alpha-hydroxy-5beta-androstan-17beta-ol | —* |
| 3alpha-hydroxy-5alpha-androstan-17-one | 53-41-8 |
| 3alpha-hydroxy-5beta-androstan-17-one | 53-42-9 |

*CAS Number not found

Some of these steroids have been shown to have an ability to induce anesthesia at a high pharmacological dose. They can also be used as anti-epileptic agents, or as soporific agents. Some of these compounds have also been shown to possess anxiolytic effects in animal experiments. To reach these effects, however, high concentrations or high doses are required. Additionally, they appear as acute effects.

With respect to their direct CNS effects, as mentioned above, these compounds are similar to benzodiazepins and barbiturates. However, they also have similar adverse effects as normally associated with benzodiazepins and barbiturates. The adverse effects of the endogenous 3alpha-hydroxy-pregnan-20-one-steroids or 3alpha-hydroxy-androstan-steroids are the basis for the negative CNS effects induced by these steroids. As the 3alpha-hydroxy-pregnane-steroids and 3alpha-hydroxy-androstan-steroids are endogenously produced and are metabolites of steroid hormones, some of them essential for life, their production cannot easily be interrupted. These steroids are produced in high amounts during several days to weeks during the luteal phase of the menstrual cycle, i.e. after the release of an ovum from a mature ovarian follicle, during pregnancy and during stress. They are also produced within the brain.

Diseases Caused by 3Alpha-Hydroxy-Steroids

Disorders that are caused by the action of endogenously produced 3alpha-hydroxy-5alpha steroids or 3alpha-hydroxy-5beta steroids on the GABA-A receptor are well characterized and understood. It is also known that 3alpha-hydroxy-5alpha/beta-steroids can induce tolerance to themselves and to other similar substances after exposure, and that withdrawal symptoms occur at withdrawal of the 3alpha-hydroxy-5alpha/beta-steroids. In summary, it is generally known that 3alpha-hydroxy-5alpha/beta-steroids cause CNS disorders through the above-described three possible mechanisms: a) direct action, b) tolerance induction, and c) withdrawal effect. These mechanisms will be discussed in closer detail below.

a) Direct Action

It is established that 3alpha-hydroxy-5alpha/beta-steroids can directly cause inhibition of CNS functions. Examples of symptoms caused by the direct action of 3alpha-hydroxy-5alpha/beta-steroids are sedation, tiredness, memory disturbance, learning disturbance, disturbance of motor function, clumsiness, increased appetite and food cravings, negative mood as tension, irritability and depression, which are the cardinal symptoms in the premenstrual dysphoric disorder, premenstrual syndrome and the worsening of Petit Mal epilepsy. Examples of this direct action can also be divided into sedative and anesthetic effects; disturbance of motor function; effects on cognitive function, memory and learning; worsening of Petit Mal epilepsy; premenstrual symptoms;

mood changes; induction of anxiety in test animals; hyperphagia and increased appetite; food cravings etc.

b) Tolerance

Continuous and long exposure to 3alpha-hydroxy-5alpha/beta-steroids causes malfunctioning of the GABA-A receptor system. A tolerance develops and this tolerance is the initial step in a process that ultimately leads to stress sensitivity, concentration difficulties, and loss of impulse control and depression. The action of 3alpha-hydroxy-5alpha/beta-steroids has also been found to be a factor, which reinforces drug dependency. This has been the focus of extensive research. The following themes have hitherto been the main subject of research: down regulation and decreased GABA function after long-term secretion of high amounts of 3alpha-hydroxy-5alpha/beta steroids; reduced benzodiazepine and 3alpha-hydroxy-5beta steroid sensitivity in PMS; and dependence induction.

c) Withdrawal Symptoms

A continuous but shorter exposure to 3alpha-hydroxy-5alpha/beta-steroids results in a withdrawal effect when the exposure is ended. This phenomenon occurs for example naturally, during menstruation when the production of 3alpha-hydroxy-5alpha/beta-steroids by the corpus luteum of the ovary is interrupted. This withdrawal phenomenon also occurs after giving birth (post partum) when the 3alpha-hydroxy-5alpha/beta-steroid production by the placenta is interrupted. The same phenomenon is also noted when a period of stress is ended, e.g. when work-related stress is interrupted during weekends. As a response to stress, the adrenals have produced 3alpha-hydroxy-5alpha/beta-steroids. When this production is interrupted, withdrawal symptoms may occur.

Examples of conditions that are influenced by this withdrawal phenomenon are partial epilepsy where the patient has an epileptic focus in the cerebral cortex where a worsening occurs at the withdrawal period during menstruation. This phenomenon is called "catamenial epilepsy". Other examples are menstrual related migraine, stress related migraine, and mood changes post partum. Similar symptoms and conditions are induced during treatment with steroid hormones, such as used in oral contraceptives, postmenopausal hormone replacement therapy, steroid treatment for inflammatory diseases and during intake of anabolic/androgenic steroids. The mechanisms are similar in the induction of direct effects, tolerance development and withdrawal.

Disorders Caused by Qamma-Aminobutyric Acid (GABA) Overstimulation

High stimulation by GABA itself is in certain situations known to inhibit learning and memory function. An overproduction of GABA will worsen short-term learning and memory function. This is clinically relevant especially in elderly people. In such a situation, an antagonism of GABA's effect could be beneficial, and potentially useful in the treatment of memory disturbance. However, if the GABA antagonism is too strong, it can be dangerous for the patient, e.g. by causing convulsions. Therefore it is of interest to find specific antagonists that selectively block the GABA-steroid induced conditions and antagonists that also affect GABA-activated chloride flux in the GABA-A receptor, but which are inherently unable to totally block the GABA-A receptor.

The present inventors have surprisingly found substances that mainly antagonize GABA's own effect and other that mainly affect GABA-steroid action on the GABA-A receptor. It is important to distinguish between these effects, as an antagonist of GABA-steroid action is indicated in other situations than a direct partial antagonism of GABA's own effect.

Currently, the treatment of Alzheimer's disease (AD) and Mild Cognitive Impairment (MCI) is largely unrealized, with no preventive or curative therapies. The fact that GABA-A receptor agonists like GABA-steroids, benzodiazepines and alcohol are amnesic, and that the GABA-A receptors in brain areas most affected by AD, highlighted the GABA-A receptor as a potential therapeutic target in AD and MCI. In contrast to the amnesic GABA-A receptor agonists, inverse agonists or antagonists will attenuate GABA-A receptors function. GABA-Steroid antagonists and GABA antagonists have been shown to improve performance in animal models of learning and memory. Unfortunately, non-selective and totally blocking ligands also induce convulsions. Thus, there is a need for partial and selective blockers (Maubach, K., GABA-A receptor subtype selective cognition enhancers, Curr. Drug Targets CNS Neurol Disord., 2003 (2) 233-239). The current cognition enhancers marketed have prominent adverse effects with minimal efficacy and there is a need for new substances, which is the subject of the present invention.

PRIOR ART

To the best knowledge of the present inventors, steroid substances that selectively inhibit GABA-steroid action or mainly inhibit GABA action on the GABA-A receptor have not been disclosed earlier. The prior art only describes a general action on all GABA-steroid effects.

Prince and Simmons (*Neuropharmacology*, vol. 32, no. 1, pp. 59-63, 1993) have used a model relying on membrane fractions of whole male rat brain. In this sub-fraction of whole brain homogenate, the authors used the binding of a benzodiazepine, 3H-flunitrazepam, as a model for steroid effect and change of GABA-A receptor conformation. This test has been suggested as an indicator of allosteric modulation of the GABA-A receptor. The relationship between the change in flunitrazepam (FNZ) binding and change in chloride flow at GABA-stimulation is however uncertain and a change in binding can not be taken as a proof of a change in the chloride flow through the GABA-receptor, nor as a proof of a change in GABA-A receptor function. The change in chloride flow is the important effect.

The central question, i.e. if there exists a relationship between change in FNZ-binding and neuronal excitability, is even less clear and such conclusions cannot be drawn from results on FNZ-binding alone. A change in FNZ-binding properties or absence of such change in binding properties does not imply a change or the absence of a change in neural activity or GABA-A mediated chloride flow.

It is also well known that the GABA-A receptor contains several sub-units that can be combined in multiple ways. Interestingly, certain combinations lack steroid recognition site. It is also known that the effect of steroid on the binding of a convulsant substance TBPS (t-butylbicyclo-phosphorothionate) differs in different brain regions. Further, it is known that the binding of TBPS varies with the oestrus cycle in female rats indicating an effect change related to the ovarian hormone production. These changes related to the oestrus cycle can of course not be noticed in male rats, as used in the studies of Prince and Simmons (supra).

U.S. Pat. No. 5,232,917 (Bolger at al.) and U.S. Pat. No. 5,939,545 (Upasani et W.) disclose a number of 3alpha-hydroxy steroids. Both these patents concern the agonistic modulation of the GABA-A receptor. In other words, these patents are both focused on the benzodiazepine-like effect of the 3alpha-hydroxy-5alpha/beta-steroids. All steroids that are modulators of the GABA-A receptor have the common feature of one 3alpha-hydroxy structure. The 3beta-hydroxy steroids mentioned in these documents were only used as controls, in order to show that the 3alpha-hydroxy-steroids were specific. Steroids with only a 3beta-hydroxy structure have never been shown to possess a GABA-A receptor modulating effect. In all cases where an effective GABA-A receptor-modulating effect is noticed, the steroid has a 3alpha-hydroxy group.

WO 99/45931 (Bäckström & Wang) discloses the antagonistic effect of one particular steroid, namely 3beta-hydroxy-5alpha-pregnan-20-one but is silent about other 3beta-hydroxy-steroids.

The antagonistic effect of 3beta-OH-5alpha-pregnan-20-one against 3alpha-OH-5alpha/beta-pregnan-20-one was first disclosed by Wang at al. (Wang M. D., Bäckström T. and Landgren S. (2000) *The inhibitory effects of allopregnanolone and pregnenolone on the population spike, evoked in the rat hippocampal CA1 stratum pyramidale in vitro, can be blocked selectively by epiallopregnanolone*. Acta Physiol Scand 169, 333-341). In that paper, a dose dependent antagonistic effect of 3beta-OH-5alpha-pregnan-20-one on two of the 3alpha-OH-5alpha/beta-steroids was shown.

WO 03/059357 (Bäckström et al.) discloses the use of pregnane steroids in the treatment of CNS disorders. This document does not mention the possibility to selectively inhibit GABA-steroid effects or the action on GABA itself.

That 3beta steroids also can have effects on the GABA's own effect was disclosed by Wang et al. (Mingde Wang, Yejun He, Lawrence N. Eisenman, Christopher Fields, Chun-Min Zeng, Jose Mathews, Ann Benz, Tao Fu, Erik Zorumski, Joe Henry Steinbach, Douglas F. Covey, Charles F. Zorumski, and Steven Mennerick. *3beta-Hydroxypregnane Steroids Are Pregnenolone Sulfate-Like GABAA Receptor Antagonists*. The Journal of Neuroscience, May 1, 2002, 22(9):3366-3375). In this paper, the authors show that when maximal stimulation of GABA-A receptors is made with GABA, certain 3beta-hydroxypregnane steroids are able to inhibit GABA's own effect. But that certain 3beta-hydroxy steroids would mainly inhibit GABA-steroid effects on GABA gated chloride flux and other steroids would also inhibit GABA's own effect was not discovered.

It remains a challenge to find specific antagonists of the 3alpha-hydroxy-pregnan-steroid action that have low GABA inhibitory effects, and to find partial antagonists of the GABA action which compounds are physiologically safe and suitable for pharmaceutical use, and which additionally are applicable in physiologically acceptable doses.

One objective of the present invention is thus to identify such specific blockers for GABA-steroid antagonism and partial antagonism towards GABA itself and to make available novel pharmaceuticals and methods for the treatment, alleviation or prevention of steroid related and/or steroid induced CNS disorders.

Further objectives, the associated solutions and their advantages will be obvious to a skilled person upon familiarizing himself with the description, examples and claims.

SUMMARY OF THE INVENTION

The present inventors have found that steroid compounds possessing a hydrogen donor in 3beta-position, in the form of a hydroxy group, and in addition have having a hydroxy group at 20 position surprisingly function as efficient blockers of the 3alpha-hydroxy-pregnan-steroid action but are minimally active against GABA itself. They have thus utility as therapeutic substances for the prevention and/or treatment of steroid related or steroid induced CNS disorders.

In addition, the present inventors have surprisingly found that pregnane steroids with an acetate group in 3 position or in 3, 20 and 21 position are able to partially inhibit GABA's own effect on the GABA mediated chloride flux. They therefore have utility, as therapeutic substances, e.g. for the prevention and/or treatment of disorders were the GABA function itself is overstimulated, as is the case in like in Alzheimer's disease.

The present inventors present four (4) compounds exhibiting low antagonism against GABA action, but with significant effect against 3alpha-hydroxy-5alpha/beta-steroid (GABA-steroid) action for use in the prevention and/or treatment of steroid related or steroid induced CNS disorders, and for the manufacture of pharmaceuticals for this purpose, namely 5alpha-PREGNAN-3beta, 20beta-DIOL, 5beta-PREGNAN-3beta, 20alpha-DIOL, 5alpha-PREGNAN-3beta, 20alpha-DIOL, 5beta-PREGNAN-3beta, 20beta-DIOL (See Table 2).

TABLE 2

List of 3beta-hydroxy-5alpha/beta-pregnan-steroids with antagonism against 3alpha-hydroxy-5alpha-pregnan-20-one enhanced GABA mediated chloride flux but with low GABA antagonism tested in the present invention.

| Substance* | Product name |
|---|---|
| 1) 5alpha-PREGNAN-3beta, 20beta-DIOL | UC1011 |
| 2) 5beta-PREGNAN-3beta, 20alpha-DIOL | UC1013 |
| 3) 5alpha-PREGNAN-3beta, 20alpha-DIOL | UC1019 |
| 4) 5beta-PREGNAN-3beta, 20beta-DIOL | UC1020 |

*The substances were obtained from Steraloids Inc., USA, and from Sigma Chemicals Co.

Further, the present inventors present ten (10) compounds exhibiting partial antagonism against GABA action for use for the prevention and/or treatment of disorders due to overstimulation by GABA and thereby induced CNS disorders, and for the manufacture of pharmaceuticals for this purpose, namely 5alpha-PREGNAN-3beta-OL-20-ONE ACETATE; 5beta-PREGNAN-3beta-OL-20-ONE; 5beta-PREGNAN-3beta, 21-DIOL-20-ONE; 5alpha-PREGNAN-3beta, 20beta-DIOL 3-ACETATE; 5beta-PREGNAN-3beta, 20beta-DIOL 3-ACETATE; 5alpha-PREGNAN-3beta, 20alpha-DIOL 3-ACETATE; 5alpha-PREGNAN-3beta, 20beta-DIOL DIACETATE; 5beta-PREGNAN-3beta, 20alpha-DIOL DIACETATE; 5beta-PREGNAN-3beta, 20beta-DIOL DIACETATE; 5beta-PREGNAN-3beta, 21-DIOL-20-ONE 21-ACETATE (See Table 3).

One aspect of the present invention is the therapeutic use of the above compounds as blocking substances against the 3alpha-hydroxy-pregnan-steroid action and GABA-action. In addition, these substances are now suggested for the manufacture of pharmaceuticals for the treatment of many specific steroid related or steroid induced CNS disorders and for use in methods of treatment, according to the attached claims, which are incorporated herein by reference.

TABLE 3

List of 3beta-hydroxy-5alpha/beta-pregnan-steroids with high GABA antagonism tested in the present invention

| Substance* | Product name |
|---|---|
| 1) 5alpha-PREGNAN-3beta-OL-20-ONE ACETATE | UC1012 |
| 2) 5beta- PREGNAN-3beta-OL-20-ONE | UC1014 |
| 3) 5beta-PREGNAN-3beta, 21-DIOL-20-ONE | UC1015 |
| 4) 5alpha-PREGNAN-3beta, 20beta-DIOL 3-ACETATE | UC1021 |
| 5) 5beta-PREGNAN-3beta, 20beta-DIOL 3-ACETATE | UC1022 |

TABLE 3-continued

List of 3beta-hydroxy-5alpha/beta-pregnan-steroids with
high GABA antagonism tested in the present invention

| Substance* | Product name |
|---|---|
| 6) 5alpha-PREGNAN-3beta, 20alpha-DIOL 3-ACETATE | UC1023 |
| 7) 5alpha-PREGNAN-3beta, 20beta-DIOL DIACETATE | UC1024 |
| 8) 5beta-PREGNAN-3beta, 20alpha-DIOL DIACETATE | UC1025 |
| 9) 5beta-PREGNAN-3beta, 20beta-DIOL DIACETATE | UC1026 |
| 10) 5beta-PREGNAN-3beta, 21-DIOL-20-ONE 21-ACETATE | UC1030 |

*The substances were obtained from Steraloids Inc., USA, and from Sigma Chemicals Co.

SHORT DESCRIPTION OF THE DRAWINGS

The intention will be described in closer detail in the following description and examples, with reference to the Tables incorporated into the description, and the attached drawings, in which.

DESCRIPTION OF THE INVENTION

Before the present invention is described, it is understood that the terminology employed herein is used for the purpose of describing particular embodiments only and is not intended to be limiting, since the scope of the present invention will be limited only by the appended claims and equivalents thereof.

In particular, it must be noted that, as used in this specification and the appended claims, the singular forms "a", "an", and "the" also include plural referents unless the context clearly dictates otherwise.

In the following description, the terms "steroid related" and "steroid induced" as in "steroid related disorders" are meant to encompass the three possible mechanisms by which steroids act on the central nervous system: a) direct action, b) tolerance induction, and c) withdrawal effect. Examples of such disorders have been given above, but they are meant to illustrate each mechanism, and not to be construed as limiting the invention.

The term "blocking" is meant to define an effect where in this case the 3alpha-hydroxy-5alpha/beta-steroids are prevented from acting on the GABA-A receptor. It is understood that "blocking" is an entirely different effect than meant by "modulation" or "repression" or similar terms, which suggest that an action is still taking place, but to a lesser extent or at a slower rate.

With the term "antagonist" is meant a substance that hinders another substance, an agonist, to induce its effect. In this application the terms antagonist and blocker are used simultaneously.

The term "pharmaceutical composition" is used in its widest sense, encompassing all pharmaceutically applicable compositions containing at least one active substance, and optional carriers, adjuvants, constituents etc. The term "pharmaceutical composition" also encompasses a composition comprising the active substance in the form of derivate or a pro-drug, such as pharmaceutically acceptable salts, sulphates and esters. The manufacture of pharmaceutical compositions for different routes of administration falls within the capabilities of a person skilled in galenical chemistry.

The terms "administration" and "mode of administration" as well as "route of administration" are also used in their widest sense. The pharmaceutical composition of the present invention may be administered in a number of ways depending largely on whether a local, topical or systemic mode of administration is most appropriate for the condition be treated. These different modes of administration are for example topical (e.g., on the skin), local (including ophthalmic and to various mucous membranes such for example vaginal and rectal delivery), oral or parenteral and pulmonary, including the upper and lower airways.

The preparation of such compositions and formulations is generally known to those skilled in the pharmaceutical and formulation arts and may be applied to the formulation of the composition of the present invention.

The present inventors have surprisingly shown that pharmaceutically suitable and practically applicable doses of steroids having a hydrogen donor in 3beta position and a hydroxy group at 20 position can inhibit the action of 3alpha-hydroxy-5alpha/beta-steroids in vitro, but have very low antagonistic effect on the effect by GABA it self. Thus they block the development of the negative effects of 3alpha-hydroxy-5alpha/beta-steroids but have minimal effects on GABA's own action. Both the mechanism of action of 3alpha-hydroxy-5alpha/beta-steroids in the development of CNS disorders and the mechanism of action of 3beta-hydroxy-5alpha/beta-pregnan or 3beta-sulfate-5alpha/delta5-pregnan/pregnen steroids in their interactions with 3alpha-hydroxy-5alpha/beta-steroids have been addressed. Examples of such compounds are given in Table 2.

In addition, the present inventors have surprisingly shown that pharmaceutically suitable and practically applicable doses of steroids having an acetate group in 3 position and/or in 3, 20 and 21 positions are able to partially inhibit GABA's own effect on GABA mediated chloride flux. These steroids therefore have utility, as therapeutic substances for the prevention and/or treatment of disorders were the GABA function it self is overstimulated like in Alzheimer's disease. Examples of such compounds are given in Table 3.

The present invention concerns all steroids having a hydrogen donor in 3beta position, in particular a hydroxy- or sulphate group and in addition has a hydroxy group at 20 position. Here exemplified by the 3beta-hydroxy-pregnan-20-ol steroids described in Table 2. The present inventors have shown that these steroids are antagonists and able to antagonize the effect of 3alpha-hydroxy-5alpha/beta-pregnan-steroids but have little effect against GABA's own effects in the central nervous system (CNS). Surprisingly, simultaneous treatment with a 3alpha-hydroxy-pregnan-steroids and 3betahydroxy-pregnan-steroids mentioned in Table 2, inhibits the chloride flux thru the GABA-A receptor recombinantly expressed in the *Xenopus lavies* oocyte induced by the 3alpha-hydroxy-pregnan-steroid but have low effect on chloride flux induced by GABA alone.

One advantage of the invention is that 3beta-hydroxy-5alpha/beta-pregnan 20-ol-steroids, in particular 5alpha-PREGNAN-3beta, 20beta-DIOL, 5beta-PREGNAN-3beta, 20alpha-DIOL, 5alpha-PREGNAN-3beta, 20alpha-DIOL, 5beta-PREGNAN-3beta, 20beta-DIOL efficiently antagonize the GABA-A receptor modulation effect of 3alpha-hydroxy-5alpha/beta-pregnan-steroids but to a low degree influences the GABA activation of the GABA-A receptor. A particular advantage is that this blocking is achieved at pharmacologically and physiologically suitable concentrations.

The new and surprising finding behind the present invention is thus that it is possible to selectively block the enhancement of GABA-activated current by 3alpha-hydroxy-5alpha/beta-pregnan-steroids by administering 3beta-hydroxy-5alpha/beta-pregnan-20-ol-steroids in pharmaceutically and physiologically acceptable amounts with none, or only minute effects on the GABA effect.

An other new and surprising finding in the present invention is that the 3beta-hydroxy-5alpha/beta-pregnan-steroids with an acetate group or groups at 3, 20 and 21 position, in particular 5alpha-PREGNAN-3beta-OL-20-ONE ACETATE; 5alpha-PREGNAN-3beta, 20beta-DIOL 3-ACETATE; 5beta-PREGNAN-3beta, 20beta-DIOL 3-ACETATE; 5alpha-PREGNAN-3beta, 20alpha-DIOL 3-ACETATE; 5alpha-PREGNAN-3beta, 20beta-DIOL DIACETATE; 5beta-PREGNAN-3beta, 20alpha-DIOL DIACETATE; 5beta-PREGNAN-3beta, 20beta-DIOL DIACETATE; 5beta-PREGNAN-3beta, 21-DIOL-20-ONE 21-ACETATE; and some 3beta-5 beta-steroids in particular 5beta-PREGNAN-3beta-OL-20-ONE, and 5beta-PREGNAN-3beta, 21-DIOL-20-ONE, are capable of partially inhibiting the direct GABA response on the GABA-A receptor. A particular advantage is that this blocking is achieved at pharmacologically and physiologically suitable concentrations.

The GABA-A receptor is a chloride channel and the GABA-A receptor exercises its action via changing the influx of chloride through the channel. It is well known in the art that the neuronal activity in the brain is decreased when the GABA-A receptor is open and a large amount of chloride flux into the cell. It is also well known that there is a relation between the amount of chloride moving in and the clinical effect of a GABA-A receptor active drug.

Benzodiazepines, barbiturates and to some extent, alcohol, exercise their action via this mechanism. This, however, also accounts for the adverse effects of these drugs. A problem with the GABA-A receptor is that is has its action in most parts of the brain. Therefore total blockers of the GABA action are dangerous and may cause psychotic symptoms and convulsions. When 3alpha-hydroxy-5alpha/beta-pregnan-steroid actions are to be antagonized, one wants to use substances that specifically antagonize 3alpha-hydroxy-5alpha/beta-pregnan-steroid effects and which do not antagonize GABA's own effect. However, in situations when the cause of the disorder is a general overactivation of the GABA-system due to the action of GABA it self a more general antagonist acting against GABA's own effect is preferred. But if these general antagonists totally block the GABA-A receptor they are dangerous.

Therefore partial antagonists like the one described in the present invention are preferred.

As has been discussed above, there are a number of symptoms and conditions that are related to 3alpha-hydroxy-5alpha/beta-pregnan-steroids, and where blocking the 3alpha-hydroxy-5alpha/beta-pregnan-steroid effect would be a treatment of the condition in question. The present inventors now make available substances and methods for such blocking.

In addition there are conditions that are related to a general overstimulation of the GABA-A system and were a partial blocker of the GABA effect would be a treatment for such conditions. The present inventors now make available substances and methods for such partial blocking of the GABA effect.

In the experimental work reported by Prince and Simmons (supra) an indirect ligand-binding assay was used. By studying the FNZ-binding alone, one can however not assume that the same effect will be seen in a neural activity in vivo. This has also not been claimed by Prince and Simmons in their paper. They have only discussed implications for binding sites of steroids and if these sites are the same or not. This is not a new discussion and the possibility of several binding sites for steroids has been indicated in earlier publications. The only conclusion drawn by them and the possible conclusions to be drawn using their experimental design and model is that the steroid changes the binding of FNZ differently and has some interactions on the FNZ-binding. No conclusion of effects on neural activity or on clinical implications can be drawn from the results of Prince and Simmons.

The present inventors have surprisingly shown that pharmaceutically suitable and useable doses of 3beta-hydroxy-5alpha/beta-pregnan-20-ol-steroids, and in particular 5alpha-PREGNAN-3beta, 20beta-DIOL 5beta-PREGNAN-3beta, 20alpha-DIOL 5alpha-PREGNAN-3beta, 20alpha-DIOL; and, 5beta-PREGNAN-3beta, 20beta-DIOL are selective blockers of the action of 3alpha-hydroxy-5alpha/beta-steroids, thus blocking the development of the negative effects of 3alpha-hydroxy-5alpha/beta-steroids but have minute effect on the GABA inhibition. The inventors have also surprisingly shown that pharmaceutically suitable and practically useable doses of 3beta-hydroxy-5alpha/beta-pregnan-steroids with an acetate group(s) in 3, 20 or 21 position, and in particular 5alpha-PREGNAN-3beta-OL-20-ONE ACETATE; 5alpha-PREGNAN-3beta, 20beta-DIOL 3-ACETATE; 5beta-PREGNAN-3beta, 20beta-DIOL 3-ACETATE; 5alpha-PREGNAN-3beta, 20alpha-DIOL 3-ACETATE; 5alpha-PREGNAN-3beta, 20beta-DIOL DIACETATE; 5beta-PREGNAN-3beta, 20alpha-DIOL DIACETATE; 5beta-PREGNAN-3beta, 20beta-DIOL DIACETATE; 5beta-PREGNAN-3beta, 21-DIOL-20-ONE 21-ACETATE and some 3beta-5 beta-steroids in particular 5beta-PREGNAN-3beta-OL-20-ONE, and 5beta-PREGNAN-3beta, 21-DIOL-20-ONE are partial blockers of the GABA effect.

The inventors have determined both the mechanisms of action behind disorders caused by 3alpha-hydroxy-5alpha/beta-steroids and GABA it self. It is well established in the art that 3alpha-hydroxy-5alpha/beta-steroids cause CNS disorders through three possible mechanisms a) direct action, b) tolerance induction, and c) withdrawal effect. It is in addition well established that a global overstimulation with GABA will eventually destroy the function of the GABA-A system and among functions deteriorating are memory and learning abilities, as known to occur e.g. in Alzheimer's disease.

Compared to previously disclosed inventions, e.g. Bolger et al., U.S. Pat. No. 5,232,917 and Upasani et al., U.S. Pat. No. 5,939,545 do not disclose any 3beta-hydroxy-5alpha/beta-pregnan-steroid as being a modulator of the GABA-A receptor, neither in the patents or in their corresponding scientific publication (Lan N. C., Gee K. W., Bolger M. B. & Chen J. S. (1991), Differential responses of expressed recombinant human gamma-aminobutyric acidA receptors to neurosteroids. *Journal of Neurochemistry,* 57(5): 1818-1821.)

Consequently, as a general aspect of the invention, the inventors make available chemical compounds capable of blocking the action of 3alpha-hydroxy-pregnan-steroids on the GABA-A receptor but not the GABA's effect as well partial antagonists on the GABA action.

Another aspect of the invention is a pharmaceutical composition comprising a compound capable of blocking the action of 3alpha-hydroxy-pregnan-steroids on the human GABA-A receptor, or a partial blocker of the GABA effect. Preferably said compound (Table 2, 3) is present in the form of a suitable and pharmaceutically acceptable salt, most preferably a sodium salt.

Another aspect of the present invention is a general method for the treatment and/or prevention of steroid related CNS disorders in human patients, wherein at least one compound capable of blocking the action of 3alpha-hydroxy-pregnan-steroids on the human GABA-A receptor is administered to said patient. Preferably said compound has a hydrogen donor in 3beta position in the form of a group chosen among a hydroxy and a sulphate group and a hydroxy group at the 20 position. Most preferably said compound is chosen among the substances given in Table 2. In addition, a general method for the treatment and/or prevention of CNS disorders in human patients related to general overstimulation of the GABA-A receptors is disclosed, wherein at least one compound capable of partially blocking the action of GABA on the human GABA-A receptor is administered to said patient. The most preferred compound is found among the compounds listed in Table 3. Preferably said compound is used in the form of a suitable and pharmaceutically acceptable salt, most preferably a sodium salt.

According to the present invention, said at least one compound is administered through one of the following routes of administration: intravenously, nasally, per rectum, intravaginally, percutaneously and orally. According to one preferred embodiment, said at least one steroid is administered intravenously. According to another preferred embodiment, said at least one steroid is administered nasally.

Nasal administration in particular is a promising alternative, as it offers the benefits of ease and the possibility of self-administration by the patient. Self-administration has the advantage of allowing the patient to adjust the dose or the frequency of medication according, either according to a subjective evaluation of their condition, or according to a schedule prescribed by the treating physician. The term "schedule prescribed by the treating physician" includes the alternative where the patient makes a subjective evaluation of his/her condition, either unaided or aided by a questionnaire or a range or scale, or using an algorithm or a computer program, indicating the suitable next dose.

Percutaneous administration, using the substances formulated as a cream, a gel, and an ointment or in the form of slow-release adhesive medicine patches, is another possible form of administration, similarly suitable for self-medication. The advantages of self-administration listed above apply also to percutaneous administration, with the added advantage that the administration can easily be interrupted if desired or necessary, e.g. by removing the medicine patch.

In any of these or other routes of administration, the formulation of the composition may be adapted or adjusted according to normal pharmacological procedures, comprising the effective pharmaceutical in a chemical form, suitable for the chosen route, together with suitable adjuvants and vehicles, conventionally used and well-known to a person skilled in the art.

Conventionally used adjuvants and vehicles for oral administration are for example fillers or suspending agents like titanium dioxide, lactose anhydride, silica, silica colloidalis, methylcellulose, magnesium stearate, microcrystalline cellulose and the like.

Conventionally used adjuvants and vehicles for intravenous administration are for example sterile water for injections (WFI), sterile buffers (for example buffering the solution to pH 7.4) albumin solution, lipid solutions and the like.

Conventionally used adjuvants and vehicles for transdermal administration are for example vaseline, liquid paraffin, glycerol, water and the like.

The dose will naturally vary depending on the mode of administration, the particular condition to be treated or the effect desired, gender, age, weight and health of the patient, as well as possibly other factors, evaluated by the treating physician. According to the present invention, when said at least one steroid is administered intravenously, a suitable interval is that of about 0.2 to 200 mg per kg body weight, preferably 0.2 to 2; 2 to 10, 10 to 20; 20 to 40; 40 to 80; 80 to 120; 120-160; and 160 to 200 mg per kg body weight. Preliminary studies in animals indicate that a preferred interval for intravenous administration is about 20 to 100 mg per kg body weight.

Corresponding dose intervals for other modes of administration may easily be calculated by a person skilled in the art, and—if necessary—verified through non-inventive animal tests or pre-clinical or clinical studies.

One embodiment of the present invention is a method for treatment of steroid related or steroid induced CNS disorders, in particular premenstrual syndrome, wherein tolerance development is prevented and the down-regulation of the GABA-A receptor prevented by administration of at least one substance according to the invention. This treatment would preserve the sensitivity of the GABA-A system and inhibit the development of a less sensitive state during the luteal phase. It has been shown in rat that there is a change of the GABA-A receptor during chronic progesterone treatment. The treatment with 3beta-hydroxy-5alpha/beta-pregnan-steroids or 3beta-sulfate-5alpha/delta5-pregnan/pregnen-steroids according to the present invention sets out to prevent the development of tolerance, and thus to hinder the withdrawal effect when the 3alpha-hydroxy-5alpha/beta-steroid is withdrawn.

A tolerance development will decrease the sensitivity for GABA-A enhancing substances endogenously produced like the 3alpha-hydroxy-5alpha-pregnan-20-one or benzodiazepins. When the drug is rapidly removed, like at the end of the luteal phase in the menstrual cycle a rebound effect arrives after the withdrawal of the 3alpha-hydroxy-5alpha-pregnan-steroids. Such a situation is found in humans with increase in migraine and epileptic seizures during the menstruation shortly after the end in production and withdrawal of the steroids.

Another embodiment of the present invention is accordingly a method for treatment or prevention of tolerance development and/or withdrawal symptoms, by administration of at least one substance according to the invention.

The present invention further concerns a method for the treatment and/or prevention of steroid related or steroid induced mood disorders in human patients described above, according to which method at least one 3beta-hydroxy-5alpha/beta-pregnan-20-ol-steroid is administered to said patient. Preferably said steroid compound is chosen among the steroids mentioned in Table 2. Most preferably said compound is used in the form of a suitable and pharmaceutically acceptable salt, most preferably a sodium salt.

Suitable routes of administration are for example the following: intravenously, nasally, per rectum, intra vaginally, percutaneously and orally.

For the treatment of many CNS disorders and for the uses as an anti-anesthetic, it is however preferred that the effective compound or compounds is/are administered intravenously.

Suitable doses according to the invention, in intravenous administration, are doses in the interval of about 0.2 to about 200 mg per kg body weight, preferably 0.2 to 2; 2 to 10, 10 to 20; 20 to 40; 40 to 80; 80 to 120; 120-160; and 160 to 200 mg per kg body weight, and most preferably about 20 to about 100 mg/kg.

As described above, the formulation of the composition may be adapted or adjusted according to normal pharmacological procedures. Further, the dose will naturally vary depending on the mode of administration, the particular condition to be treated or the effect desired, the gender, age, weight and health of the patient, as well as possibly other factors, evaluated by the treating physician.

Further, the present invention encompasses methods for the treatment and/or prevention of steroid related or steroid induced CNS disorders in human patients, according to which method one or more 3beta-hydroxy-5alpha/beta-pregnan-20-ol-steroids (see Table 2) is/are administered in a pharmaceutically and physiologically acceptable dose to said patient. Preferably said steroid compound is chosen among the steroids in Table 2. Most preferably said compound is used in the form of a suitable and pharmaceutically acceptable salt, most preferably a sodium salt.

Examples of symptoms and conditions caused by the direction action of 3alpha-hydroxy-5alpha/beta-steroids are sedation, tiredness, memory disturbance, learning disturbance, disturbance of motor function, clumsiness, increased appetite and food cravings, negative mood as tension, irritability and depression which are the cardinal symptoms in the premenstrual syndrome and the worsening of Petit Mal epilepsy.

Conditions and symptoms caused by tolerance development after long time (days) exposure to 3alpha-hydroxy-5alpha/beta-steroids are e.g. stress sensitivity, concentration difficulties, stress or menstrual cycle linked difficulties in concentration, sleep disorders, tiredness, loss of impulse control and depression. 3alpha-hydroxy-5alpha/beta-steroids also reinforce drug dependency. According to the present invention, these conditions or symptoms can be prevented, alleviated or treated by the administration of at least one 3beta-hydroxy-5alpha/beta-pregnan-20-ol-steroid to the patient. Preferably said steroid compound is chosen among the steroids in Table 2. Most preferably said compound is used in the form of a suitable and pharmaceutically acceptable salt, most preferably a sodium salt.

A continuous but shorter exposure to 3alpha-hydroxy-5alpha/beta-steroids gives a withdrawal effect when the exposure is ended. This phenomenon occurs during menstruation when the production of 3alpha-hydroxy-5alpha/beta-steroids by the corpus luteum of the ovary is interrupted. This withdrawal phenomenon also occurs after giving birth (post partum) when the 3alpha-hydroxy-5alpha/beta-steroid production by the placenta is interrupted. The same phenomenon is also noted when a period of stress is ended and the 3alpha-hydroxy-5alpha/beta-steroids produced by the adrenal during the stress are interrupted. Examples of conditions that are influenced by this withdrawal/abstinence phenomenon are partial epilepsy where the patient has an epileptic focus in the cerebral cortex where a worsening occurs at the withdrawal period during menstruation. This phenomenon is called "catamenial epilepsy". Other examples are menstrual related migraine and stress related migraine and mood changes post partum. Withdrawal symptoms is a sign of an earlier developed tolerance.

Examples of such disorders, believed to be steroid related or steroid induced, include the following: epilepsy, menstruation cycle dependent epilepsy, depression, stress related depression, migraine, tiredness and in particular stress related tiredness, premenstrual syndrome, premenstrual dysphoric disorder, menstrual cycle linked mood changes, menstrual cycle linked memory changes, stress related memory changes, menstrual cycle linked difficulties in concentration, menstrual cycle linked sleep disorders and tiredness. There are strong indications that also obesities and increased appetite, as well as some forms of balance disturbances, alcohol and substance abuse are steroid related or steroid induced. The present invention thus offers substances and methods for treatment, alleviation or prevention of these conditions.

One preferred embodiment of the invention, addressing a problem afflicting numerous women, is a method for the treatment and/or prevention of side effects of postmenopausal therapy in human patients, according to which method at least one 3beta-hydroxy-5alpha/beta-pregnan-20-ol-steroid is administered to said patient. Preferably said steroid compound is chosen among the steroids mentioned in Table 2. Most preferably said compound is used in the form of a suitable and pharmaceutically acceptable salt, most preferably a sodium salt.

Another preferred embodiment of the invention is the treatment and/or prevention of side effects of oral contraceptives in human patients, in which treatment at least one 3beta-hydroxy-5alpha/beta-pregnan-20-ol-steoid is administered to said patient. Preferably said steroid compound is chosen among the steroids in Table 2. Most preferably said compound is used in the form of a suitable and pharmaceutically acceptable salt, most preferably a sodium salt.

In this application, it is preferred, that the effective composition of at least one of the above exemplified 3beta-hydroxy-5alpha/beta-pregnan-steroids or a 3beta-sulfate-5alpha/delta5-pregnan/pregnen-steroids is/are administered together with the oral contraceptive, taken by the patient. Nasal and percutaneous administrations are also suitable routes of administration.

One particular embodiment of the present invention is thus a pharmaceutical composition comprising an oral contraceptive and a therapeutically suitable dose of at least one chemical compound capable of blocking the action of 3alpha-hydroxy-pregnan-steroids on the human GABA-A receptor, wherein said compound/-s has/have a hydrogen donor in 3beta position in the form of a group chosen among hydroxy and sulphate groups and a hydroxy group in 20 position. Preferably said compound is chosen among the steroids in Table 2. Most preferably said compound is used in the form of a suitable and pharmaceutically acceptable salt, most preferably a sodium salt.

Further, within the scope of the above embodiment, the dose of the chemical compound capable of blocking the action of 3alpha-hydroxy-pregnan-steroids on the human GABA-A receptor is preferably adjusted to the levels of endogenous steroids during stress or the menstrual period. According to the invention, a chemical compound capable of blocking the action of 3alpha-hydroxy-pregnan-steroids on the human GABA-A receptor may included in an oral contraceptive both in order to alleviate or remove the side-effects of oral contraceptives, or in order to alleviate or remove any unwanted effect of the periodical changes in endogenous steroids.

In general, the present invention encompasses the use of 3beta-hydroxy-5alpha/beta-pregnan-20-ol-steroid and in particular the steroids mentioned in Table 2, either alone or in combination, for the manufacture of a pharmaceutical for the treatment or prevention of any one of the 3alpha-hydroxy-5alpha/beta-pregnan-steroid related or—induced disorders described in the specification, and especially one or several of the following disorders: epilepsy, menstruation cycle dependent epilepsy, depression, stress related depression, migraine, tiredness and in particular stress related tiredness, premenstrual syndrome, premenstrual dysphoric disorder, menstrual cycle linked mood changes, menstrual cycle linked memory changes, stress related memory changes, menstrual cycle linked difficulties in concentration, menstrual cycle linked sleep disorders and tiredness. Preferably said compound is used in the form of a suitable and pharmaceutically acceptable salt, most preferably a sodium salt.

Another preferred embodiment of the invention is a method of treatment and/or prevention of disorders caused by gamma-aminobutyric acid (GABA) overstimulation by the use of 3beta-hydroxy-5alpha/beta-pregnan-steroids with acetate group or groups at 3, 20 and 21 positions and some 3beta-hydroxy-5 beta-pregnan-steroids.

High stimulation of the GABA-A receptor by GABA itself is in certain situations known to inhibit learning and memory function. An overstimulation of the GABA-A receptor system will worsen short-term learning and memory function and this is clinically relevant in especially elderly people. In such a situation an antagonism of GABA's effect would be beneficial can be used as treatment of memory disturbance. However, if the GABA antagonism is too strong it will be dangerous and cause convulsions. Therefore antagonists that partly antagonizes GABA induced changes in the GABA-A receptor but do not totally block the GABA-A receptor are preferred. Further, the present invention encompasses methods for the treatment and/or prevention of CNS disorders in human patients induced by general overstimulation of the GABA-A receptor system, according to which method one or more 3beta-hydroxy-5alpha/beta-pregnan-steroids with acetate group or groups at 3, 20 and 21 positions and some 3beta-hydroxy-5 beta-pregnan-steroids (see Table 3) is/are administered in a pharmaceutically and physiologically acceptable dose to said patient. Preferably said steroid compound is chosen among the steroids 5alpha-PREGNAN-3beta-OL-20-ONE ACETATE; 5alpha-PREGNAN-3beta, 20beta-DIOL 3-ACETATE; 5beta-PREGNAN-3beta, 20beta-DIOL 3-ACETATE; 5alpha-PREGNAN-3beta, 20alpha-DIOL 3-ACETATE; 5alpha-PREGNAN-3beta, 20beta-DIOL DIACETATE; 5beta-PREGNAN-3beta, 20alpha-DIOL DIACETATE; 5beta-PREGNAN-3beta, 20beta-DIOL DIACETATE; 5beta-PREGNAN-3beta, 21-D10L-20-ONE 21-ACETATE, 5beta-PREGNAN-3beta-OL-20-ONE, and 5beta-PREGNAN-3beta, 21-DIOL-20-ONE as listed in Table 3. Most preferably said compound is used in the form of a suitable and pharmaceutically acceptable salt, most preferably a sodium salt. A particular advantage is that this blocking is achieved at pharmacologically and physiologically suitable concentrations.

Examples of such disorders, believed to be related to or induced by an overstimulation of the GABA-A system, include Alzheimer's disease (AD) and Mild Cognitive Impairment (MCI) especially in elderly. The present invention thus offers substances and methods for treatment, alleviation or prevention of these conditions.

EXAMPLES

The present invention is based on experiments in vitro, performed to confirm the specificity in the diverted effects on blocking the 3alpha-hydroxy-5alpha/beta-pregnan-steroid enhanced GABA mediated chloride flux and the blocking effect on the response of GABA's own effect. The results from the in vitro tests in recombinant GABA-A receptors expressed in the surface of *Xenopus laevis* oocytes are confirmed in tests using cortical tissue from male rats performed by the inventors.

Studies of Chloride Flux in Recombinant GABA-A Receptors (Alpha1, Beta2, Gama2L) Expressed in *Xenopus laevis* Oocytes Using Voltage Clamp Methods.

Figure 1:
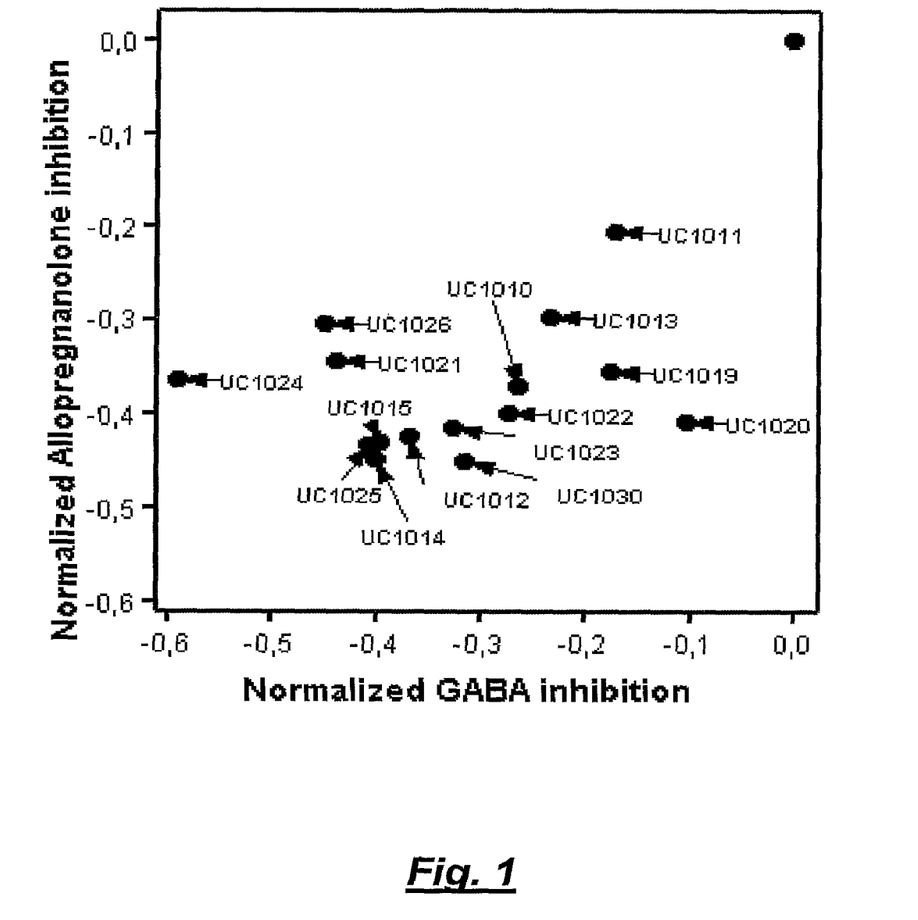
FIG. 1 shows a relation between inhibition of maximal GABA mediated chloride flux (30 µM GABA) and inhibition of 3alpha-hydroxy-5alpha-pregnan-20-one enhanced GABA mediated chloride flux in recombinant GABA-A receptors (alpha1, beta2, gamma2L) expressed in Xenopus lavies oocyctes. The labels of the data points are marked with product numbers, whereas the numbering correlated to the full name is shown in Tables 2 and 3. The black cross (X) highlights the steroid antagonist that inhibits 3alpha-hydroxy-5alpha-pregnan-20-one (3 µM) enhanced GABA (3 µM) response. The black dots (●) highlight the steroid antagonist that inhibits both direct GABA-response (30 µM) and 3alpha-hydroxy-5alpha-pregnan-20-one enhanced GABA response.

The GABA-A receptor used to test the steroids in the present invention was recombinantly expressed in oocytes of *Xenopus laevis*. The oocytes have a large capacity to express proteins for the surface membrane from mRNA injected into the oocyte. The receptor contains five proteins of three different types and the mRNA for the receptor subtypes alpha1, beta2, gamma2L were expressed in the present test situation. These subtypes of the GABA-A receptor are the most common in the central nervous system. These GABA-A receptors contain two alpha1 proteins, two beta2 and one gamma protein. After 48 hours of incubation the GABA-A receptors are mounted in the membrane and behave in vitro in a similar way as the receptor in situ. Therefore this model system is considered by persons skilled in art to be a good in vitro test system for GABA-A receptor active drugs. The flux of chloride through the chloride channel is a result of GABA activity on the GABA-A receptor and GABA-A receptor modulators like the 3alpha-hydroxy-5alpha/beta-pregnan-steroids can enhance the effectiveness of GABA. The flux of chloride through the receptor is measured as the current induced by the flux with a voltage clamp technique. Dose response curves of the agonists and antagonists can be developed and the current is dependent of the GABA-A receptor activation obtained after the interaction between different dosages of agonists and antagonists. By normalizing the data against a precise current, in the present study 2 µA, the results from different oocytes can be compared and by normalizing the current change against a specific dose, here 10 µM, the different test substances can be compared. The 3alpha-hydroxy-5alpha-pregnan-20-one induced enhancement of GABA mediated chloride flux was set to 1 and obtained by superfusing the GABA-A receptor expressing oocytes with 3 µM GABA+3 µM 3alpha-hydroxy-5alpha-pregnan-20-one in an in vitro bath. The chloride flux was measured as the current induced by the flux of chloride through the GABA-A receptors. The GABA induced chloride flux was set to 1 and obtained by superfusing the GABA-A receptor expressing oocytes in vitro with 30 µM GABA. The inhibiting effect on 3alpha-hydroxy-5alpha-pregnan-20-one induced enhancement of GABA mediated chloride flux by the tested UC-steroids is compared to the inhibiting effect of the same UC-steroids on GABA activation of the GABA-A receptor. The results are shown in FIG. 1 and Table 4. In FIG. 1 are the UC-steroids with low GABA antagonism highlighted with an X while the UC-steroids with partial GABA antagonism are highlighted with a black dot (●).

FIG. 1 shows a relation between inhibitions of maximal GABA mediated chloride flux (30 µM GABA), X-axes, and inhibition of 3alpha-hydroxy-5alpha-pregnan-20-one enhanced GABA mediated chloride flux, Y-axes, in recombinant GABA-A receptors (alpha1, beta2, gamma2L) expressed in *Xenopus laevis* oocytes. On the figure the result are normalized to the control currents activated by 30 M GABA or 3 μM GABA+3 μM 3alpha-hydroxy-5alpha-pregnan-20-one. The control current in the absence of steroid antagonists is normalized to 0. Each steroid antagonist is tested at 10 μM. The black crosses (X) highlights the steroids exhibiting low GABA inhibition but significantly inhibits 3alpha-hydroxy-5alpha-pregnan-20-one enhanced GABA mediated response. The black dot (●) highlights the steroid antagonist that inhibits both direct GABA-response (30 μM) and 3alpha-hydroxy-5alpha-pregnan-20-one enhanced GABA response. The labels of the data points are marked with product numbers, whereas the numbering of different substances full name is shown in Table 2 and Table 3.

Table 4 gives a summary of the tested UC-steroid antagonistic effect on 3 μM GABA+3 μM 3alpha-hydroxy-5alpha-pregnan-20-one stimulated chloride flux as well as on 30 μM GABA stimulated chloride flux. Tested for antagonism are the 3beta-hydroxy-5alpha/beta-pregnan-20-hydroxy-steroids and 3beta-hydroxy-5alpha/beta-pregnan-steroids with acetate group or groups at 3, 20 and 21 positions and some 3beta-hydroxy-5 beta-pregnan-steroids shown in Table 2 and 3. Some of the steroids, (5alpha ALPHA-PREGNAN-3beta-OL-20-ONE, UC1010; 5alpha-PREGNAN-3beta, 20beta-DIOL, UC1011; 5alpha-PREGNAN-3beta-OL-20-ONE ACETATE, UC1012; 5beta-PREGNAN-3beta, 20alpha-DIOL, UC1013; 5beta-PREGNAN-3beta-OL-20-ONE, UC1014; 5beta-PREGNAN-3beta, 21-DIOL-20-ONE, UC1015) has previously been disclosed in patent applications WO 99/45931 and WO 03/059357 and are included here only for the sake of completeness. Some of the steroids disclosed in WO 03/059357 have now been discovered to have additional effects namely having low antagonism against GABA it self (5alpha-PREGNAN-3beta, 20beta-DIOL, UC1011; 5beta-PREGNAN-3beta, 20alpha-DIOL, UC1013) while others have now been discovered to have a partial antagonism against the GABA effect (5alpha-PREGNAN-3beta-OL-20-ONE ACETATE, UC1012; 5beta-PREGNAN-3beta-OL-20-ONE, UC1014; 5beta-PREGNAN-3beta, 21-DIOL-20-ONE, UC1015).

TABLE 4

Mean normalized-1 antagonism of UC substances, 10 μM, against 3alpha-hydroxy-5alpha-pregnan-20-one + GABA or GABA alone stimulated chloride current through the rat GABA-A receptor expressed in *Xenopus laevis* oocytes as alpha1, beta2, gamma2L.

| UC code | Mean Normalized-1 3alpha-hydroxy-5alpha-pregnan-20-one Inhibition | Mean Normalized-1 GABA Inhibition |
|---|---|---|
| GABA alone | .00 | .00 |
| 3alpha-hydroxy-5alpha-pregnan-20-one | | |
| UC1010 | −.37 | −.26 |
| UC1011 | −.21 | −.17 |
| UC1012 | −.42 | −.37 |
| UC1013 | −.30 | −.23 |
| UC1014 | −.45 | −.39 |
| UC1015 | −.43 | −.40 |
| UC1019 | −.36 | −.17 |
| UC1020 | −.41 | −.10 |
| UC1021 | −.34 | −.44 |
| UC1022 | −.40 | −.27 |
| UC1023 | −.42 | −.32 |
| UC1024 | −.36 | −.59 |
| UC1025 | −.43 | −.41 |
| UC1026 | −.30 | −.45 |
| UC1030 | −.45 | −.31 |

The studies on 3alpha-hydroxy-5alpha-pregnan-20-one inhibition were made in the presence of 3 μM GABA+3 μM 3alpha-hydroxy-5alpha-pregnan-20-one. The studies on GABA antagonism were made with the dosage of 100 μM GABA. The current in the recordings were normalized against a stimulation of 2 μAmpere and the mean effect displayed in the Table are normalized −1 against 3 μM 3alpha-hydroxy-5alpha-pregnan-20-one and 100 μM GABA, respectively. Number of cells recorded n=3-10.

Cortical Tissue Homogenate Study

Some of the steroids (see FIG. 2) investigated in the *Xenopus* oocyce model have also been tested by the present inventors on the ability to inhibit the effect of 3alpha-hydroxy-5alpha/beta-pregnan-steroids in a GABA-A receptor model of chloride uptake. The GABA-A receptors used in the chloride uptake experiments were collected from rat cortical tissue, which is a representative part of the brain for measurement of GABA-A receptor effects. As the results with the two techniques are very similar it can be assumed, with a high degree of confidence, that the results achieved in this model can be confirmed in higher mammals and in human patients.

In these studies, cortical tissue from mature male rats was homogenized in buffer. As a result of this procedure a suspension of small vesicles was formed, said vesicles having GABA-A receptors on their surface. When radioactive chloride is added to this suspension, a certain amount will enter the vesicles. This amount is related to how open the GABA-A receptor is. Drugs that open the receptor will increase the amount of chloride in the vesicles in relation to the dosage of the drug. Similarly, drugs that close the GABA-A receptor will decrease the amount of chloride moving into the vesicles. The labeled chloride outside of the vesicles was washed away and separated from the chloride inside. The amount of radioactively labeled chloride inside the vesicles was thereafter measured in a fluid scintillator and a curve drawn. At each experiment, a control of increasing dosages of GABA was used to ensure that the tissue sample is working properly. A second control was used were a full dose response curve with 3alpha-hydroxy-5alpha-pregnano-20-one +10 μM of GABA was constructed.

Figure 2:
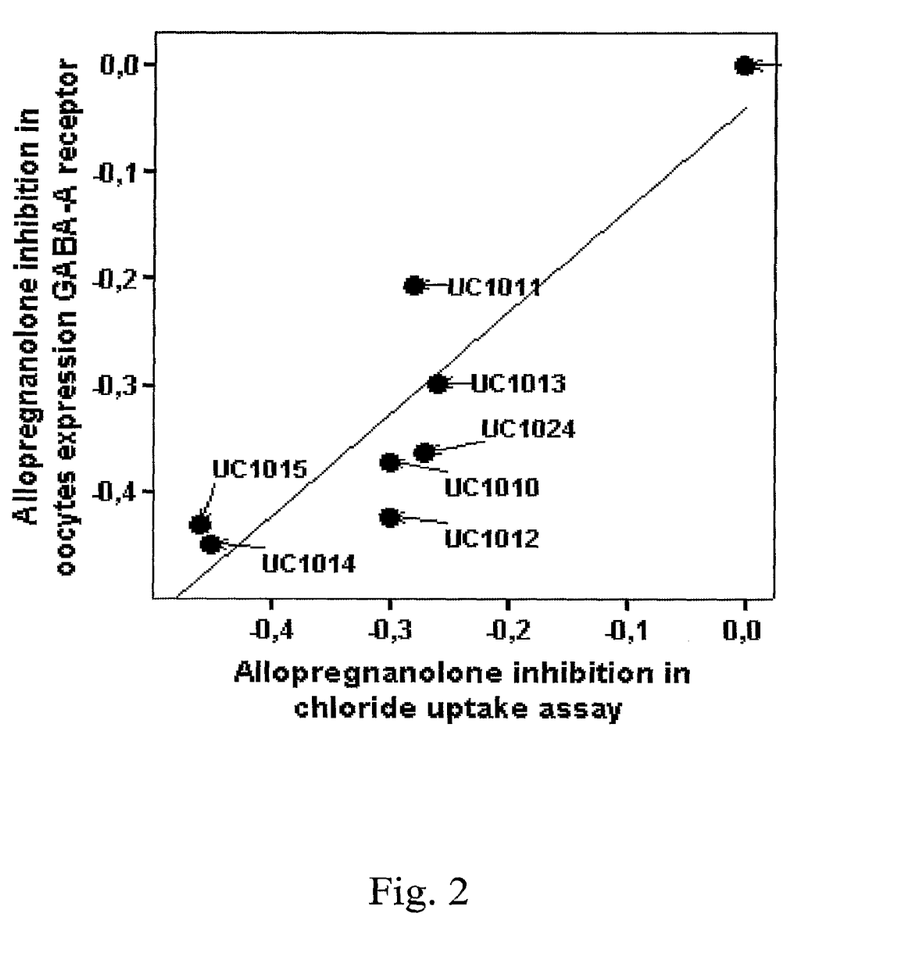
FIG. 2 shows the relation between inhibition of 3alpha-hydroxy-5alpha-pregnan-20-one enhancement of GABA mediated chloride flux in recombinant GABA-A receptors (alpha1, beta2, gamma2L) expressed in Xenopus lavies oocyctes and inhibition of 3alpha-hydroxy-5alpha-pregnan-20-one enhanced GABA mediated chloride uptake in cortical micros sacs from male rat cortex. The data points are marked with product names, and the full names are shown in Tables 2 and 3.

FIG. 2 shows the relation between inhibition of 3alpha-hydroxy-5alpha-pregnan-20-one enhancement of GABA mediated chloride flux in recombinant GABA-A receptors (alpha1, beta2, gamma2L) expressed in *Xenopus laevis* oocyctes and inhibition of 3alpha-hydroxy-5alpha-pregnan-20-one enhanced GABA mediated chloride uptake in cortical micros sacs from male rat cortex. Data in on the X and Y axes are given as the normalized value −1 to show the inhibitory effect by the separate substances. The effect of 3 μM GABA+3 μM 3alpha-hydroxy-5alpha-pregnan-20-one was set to 0 for the oocyte data. Each steroid is tested at 10 μM. The data in the chloride uptake assay were normalized against the effect of 10 μM GABA+1 μM 3alpha-hydroxy-5alpha-pregnan-20-one which was set as=0. Each steroid is tested at 30 μM. The labels of the points are product numbers, while the different substances full name is shown in Table 2 and 3. The regression line for the relation gives normalized −1 3alpha-hydroxy-5alpha-pregnan-20-one inhibition in oocyte=−0.04+0.96*

Normalized −1 chloride uptake in cortical microsacs. Pearson's correlation coefficient r=0.90; p<0.002. The two different methods for showing the inhibitory properties of the UC-steroids give highly correlated results. The results indicate that the differences in steroid effects are real.

The GABA-A receptor used to test the steroids in the present invention was recombinantly expressed in oocytes of *Xenopus laevies*. The oocytes have a large capacity to express proteins for the membranes from mRNA injected into the oocyte. The receptor contains three different proteins and the mRNA for the receptor subtypes alpha1, beta2, gamma2L were expressed in the present test situation. These subtypes of the GABA-A receptor are the most common in the central nervous system. These GABA-A receptors behave in vitro in a similar way as the receptor in situ and is therefore by the persons skilled in art considered to be a good in vitro test system for GABA-A receptor active drugs. The flux of chloride through the chloride channel is a result of GABA activity on the GABA-A receptor and the effectiveness of GABA can be enhanced by GABA-A receptor modulators like the 3alpha-hydroxy-5alpha/beta-pregnan-steroids. The current created by the flux of chloride through the receptor is measured with a voltage clamp technique. Dose response curves can be developed and by normalizing the data against a precise current, in the present study 2 µA, the results from different oocytes can be compared and by normalizing against a specific dose, in this case 10 µM, the different test substances can be compared. The inhibiting effect on 3alpha-hydroxy-5alpha-pregnan-20-one induced enhancement of GABA mediated chloride flux by the tested UC-steroids is compared to the inhibiting effect of the same UC-steroids on GABA activation of the GABA-A receptor. The results are shown with different labels in FIG. 1. Some of the steroids (se FIG. 2) investigated in the *Xenopus* oocyte model have also been shown by the present inventors to inhibit the effect of 3alpha-hydroxy-5alpha/beta-pregnan-steroids in a GABA-A receptor model of chloride uptake. The GABA-A receptors used in the chloride uptake experiments were collected from rat cortical tissue, which is a representative part of the brain for measurement of GABA-A receptor effects. It can be assumed, with a high degree of confidence, that the results achieved in this model can be confirmed in higher mammals and in human patients.

Although the invention has been described with regard to its preferred embodiments, which constitute the best mode presently known to the inventors, it should be understood that various changes and modifications as would be obvious to one having the ordinary skill in this art may be made without departing from the scope of the intention which is set forth in the claims appended hereto.

What is claimed is:

1. A method for the treatment and/or alleviation of one or more CNS disorders where the gamma-aminobutyric acid (A) receptor (GABA-A) is involved, selected from the group consisting of: obesity, epilepsy, menstruation cycle dependant epilepsy, depression, stress related depression, migraine, tiredness, stress related tiredness, premenstrual syndrome, premenstrual dysphoric disorder, menstrual cycle linked mood changes, menstrual cycle linked memory changes, stress related memory changes, menstrual cycle linked difficulties in concentration, menstrual cycle linked sleep disorders and tiredness, stress sensitivity, concentration difficulties, stress or menstrual cycle linked difficulties in concentration, sleep disorders, loss of impulse control, sedation, memory disturbance, learning disturbance, clumsiness, increased appetite and food cravings, negative mood as tension, irritability, side effects of postmenopausal therapy, and side effects of oral contraceptives, characterized in that the effect on the GABA-A receptor is controlled through administering to a patient in need thereof a substance which inhibits 3alpha-hydroxy-5alpha/beta-steroid action substantially without antagonistic effect on the GABA action on the receptor, wherein the substance is 5alpha-PREGNAN-3beta, 20alpha-DIOL or 5beta-PREGNAN-3beta, 20beta-DIOL.

2. The method according to claim 1, wherein said substance is 5alpha-PREGNAN-3beta, 20alpha-DIOL.

3. The method according to claim 1, wherein said substance is 5beta-PREGNAN-3beta, 20beta-DIOL.

4. A method for the treatment and/or alleviation of a CNS disorder where the gamma-aminobutyric acid (A) receptor (GABA-A) is involved, wherein the CNS disorder is obesity, characterized in that the effect on the GABA-A receptor is controlled through the use of a substance which inhibits 3alpha-hydroxy-5alpha/beta-steroid action substantially without antagonistic effect on the GABA action on the receptor, wherein the substance is 5alpha-PREGNAN-3beta, 20alpha-DIOL or 5beta-PREGNAN-3beta, 20beta-DIOL.

5. The method according to claim 4, wherein said substance is 5alpha-PREGNAN-3beta, 20alpha-DIOL.

6. The method according to claim 4, wherein said substance is 5beta-PREGNAN-3beta, 20beta-DIOL.

* * * * *